US006595927B2

(12) United States Patent
Pitts-Crick et al.

(10) Patent No.: US 6,595,927 B2
(45) Date of Patent: Jul. 22, 2003

(54) METHOD AND SYSTEM FOR DIAGNOSING AND ADMINISTERING THERAPY OF PULMONARY CONGESTION

(75) Inventors: Jonathan Pitts-Crick, Bristol (GB); Geeske Van Oort, Rosmalen (NL)

(73) Assignee: Medtronic, Inc., Minneapolis, MN (US)

( * ) Notice: Subject to any disclaimer, the term of this patent is extended or adjusted under 35 U.S.C. 154(b) by 67 days.

(21) Appl. No.: 09/909,960

(22) Filed: Jul. 23, 2001

(65) Prior Publication Data

US 2003/0023184 A1 Jan. 30, 2003

(51) Int. Cl.⁷ ................................................. A61B 5/00
(52) U.S. Cl. .......................... 600/529; 600/547; 607/17
(58) Field of Search ................................. 600/547, 529, 600/508, 513; 607/17–23

(56) References Cited

U.S. PATENT DOCUMENTS

| | | |
|---|---|---|
| 3,923,060 A | 12/1975 | Ellinwood |
| 4,003,379 A | 1/1977 | Ellinwood |
| 4,316,472 A | 2/1982 | Mirowski et al. |
| 4,360,031 A | 11/1982 | White |
| 4,375,817 A | 3/1983 | Engle |
| 4,379,459 A | 4/1983 | Stein |
| 4,384,585 A | 5/1983 | Zipes |
| 4,566,063 A | 1/1986 | Zolnowsky et al. |
| 4,577,633 A | 3/1986 | Berkovits et al. |
| 4,587,970 A | 5/1986 | Holley et al. |
| 4,726,380 A | 2/1988 | Vollmann |
| 4,727,877 A | 3/1988 | Kallok |
| 4,800,883 A | 1/1989 | Winstrom |
| 4,821,723 A | 4/1989 | Baker et al. |
| 4,830,006 A | 5/1989 | Haluska |
| 4,880,005 A | 11/1989 | Pless et al. |
| 4,949,719 A | 8/1990 | Pless et al. |
| 4,953,551 A | 9/1990 | Mehra |
| 5,131,388 A | 7/1992 | Pless et al. |
| 5,144,949 A | 9/1992 | Olson |
| 5,158,078 A | 10/1992 | Bennett et al. |

(List continued on next page.)

OTHER PUBLICATIONS

"Onset and Stability for Ventricular Tachyarrhythmia Detection in an Implantable Pacer–Cardioverter–Defibrillator" Olson et al., Computers in Cardiology, Oct. 7–10, 1986, IEEE Computer Society Press, pp 167–170.

*Primary Examiner*—Robert L. Nasser
(74) *Attorney, Agent, or Firm*—Thomas F. Woods; Eric R. Waldkoetter; Thomas G. Berry

(57) ABSTRACT

A method of diagnosing pulmonary congestion is provided. At least one decrease in a trans-thoracic impedance value from a baseline trans-thoracic impedance value is sensed. At least one increase in a heart rate value from a baseline heart rate value is also sensed. Pulmonary congestion is diagnosed if the decrease in the trans-thoracic impedance value corresponding to the increase in the heart rate does not increase after a predetermined interval. Systems and programs incorporating the method are also provided.

73 Claims, 8 Drawing Sheets

U.S. PATENT DOCUMENTS

| | | |
|---|---|---|
| 5,163,427 A | 11/1992 | Keimel |
| 5,188,105 A | 2/1993 | Keimel |
| 5,199,428 A | 4/1993 | Obel et al. |
| 5,207,218 A | 5/1993 | Carpentier |
| 5,213,098 A | 5/1993 | Bennett et al. |
| 5,269,298 A | 12/1993 | Adams et al. |
| 5,312,453 A | 5/1994 | Shelton et al. |
| 5,314,430 A | 5/1994 | Bordy |
| 5,330,507 A | 7/1994 | Schwartz |
| 5,331,966 A | 7/1994 | Bennett et al. |
| 5,354,316 A | 10/1994 | Keimel |
| 5,405,362 A | 4/1995 | Kramer |
| 5,454,377 A | 10/1995 | Dzwonczyk |
| 5,545,186 A | 8/1996 | Olson |
| 5,566,063 A | 10/1996 | Gerster et al. |
| 5,690,686 A | 11/1997 | Min et al. |
| 5,800,456 A | 9/1998 | Maeda et al. |
| 5,807,272 A | 9/1998 | Kun et al. |
| 6,104,949 A | 8/2000 | Pitts-Crick et al. |
| 6,473,640 B1 * | 10/2002 | Erlebacher .................. 600/547 |
| 6,511,438 B2 * | 1/2003 | Bernstein et al. ........... 600/526 |
| 6,512,949 B1 * | 1/2003 | Combs et al ............... 600/547 |

* cited by examiner

METHOD AND SYSTEM FOR DIAGNOSING AND ADMINISTERING THERAPY OF PULMONARY CONGESTION

FIELD OF THE INVENTION

The present invention relates to medical devices, systems and methods, and, more particularly, to a method and system for diagnosing pulmonary congestion in a mammalian heart.

BACKGROUND OF THE INVENTION

Pulmonary congestion is a condition that affects thousands of people throughout the world. Pulmonary congestion may be described as the inability of the heart to pump blood at an adequate rate in response to the filling pressure. Such a condition can have many consequences, including congestion in the tissues, peripheral as well as pulmonary edema, and shortness of breath. In its most severe stages, congestive heart failure results in death.

For this reason, many approaches to treating pulmonary congestion have been tried. These past attempts include electrical stimulation as well as drug therapy or both in combination. See for example, U.S. Pat. No. 5,213,098 to Bennett et al. (electrical stimulation) or U.S. Pat. No. 5,405,362 to Kramer, U.S. Pat. No. 4,360,031 to White, U.S. Pat. No. 3,923,060 or 4,003,379 to Ellinwood (electrical stimulation and drug therapy).

To date drug therapy is the method of treatment that has enjoyed the greatest success. Such drug therapies include, for example, diuretic agents and angiotens in converting enzyme inhibitors. One particular method, which has been found to be somewhat effective in reducing the symptoms of pulmonary congestion, is intermittent administration of nitroglycerin to the body.

Although various drug therapies may be effective in select patients, in many cases such a treatment has limited effectiveness or is difficult to administer or both. For example, nitroglycerin is only effective if administered at the appropriate and may also lead to a number of side effects including hypotension; administration of nitroglycerin also usually requires physician supervision.

Attempts have been made to use external impedance measuring systems to detect ischemia, which can lead to pulmonary congestion. For example, Kun et al., U.S. Pat. No. 5,807,272 discloses an impedance spectroscopy tissue status monitoring and measurement system. Likewise, Dzwonczyk et al., U.S. Pat. No. 5,454,377 discloses a method for measuring the complex impedance spectrum of a portion of the myocardium. However, both inventions do not measure the trans-thoracic impedance of the patient. U.S. Pat. No. 5,282,840 to Hurdlik discloses a physiological monitoring system for monitoring the condition of a patient's body tissue. U.S. Pat. No. 6,104,949 to Pitts-Crick and Van Oort, discloses a device and method useful in the diagnosis and treatment of congestive heart failure, which senses trans-thoracic impedance as well as patient posture and is incorporated herein by reference.

Thus it would be desirable to provide a way to detect and quantitatively monitor the degree of pulmonary congestion. Such a quantitative monitor should be sensitive to early changes of pulmonary congestion, should be both easy and convenient to use, and should require little or no physician supervision. It would also be desirable to provide an automatic method and device for treating pulmonary congestion that uses such a quantitative monitor.

As discussed above, the most pertinent prior art patents are shown in the following table:

TABLE 1

| Prior Art Patents. | | |
|---|---|---|
| U.S. Pat. No. | Date | Inventor(s) |
| 3,923,060 | Jan. 1, 1976 | Ellinwood |
| 4,003,379 | Jan. 18, 1977 | Ellinwood |
| 4,360,031 | Nov. 23, 1982 | White |
| 5,213,098 | May 25, 1993 | Bennett et al. |
| 5,282,840 | Feb. 1, 1994 | Hudrlik |
| 5,405,362 | Apr. 11, 1995 | Kramer |
| 5,454,377 | Oct. 3, 1995 | Dzwonczyk et al. |
| 5,807,272 | Sep. 15, 1998 | Kun et al. |
| 6,104,949 | Aug. 15, 2000 | Pitts-Crick et al. |

All the patents listed in Table 1 are hereby incorporated by reference herein in their respective entireties. As those of ordinary skill in the art will appreciate readily upon reading the Summary of the Invention, the Detailed Description of the Preferred Embodiments and the claims set forth below, many of the devices and methods disclosed in the patents of Table 1 may be modified advantageously by using the teachings of the present invention.

SUMMARY OF THE INVENTION

The present invention is therefore directed to providing a method and system for diagnosing and/or measuring ischemia and/or pulmonary congestion. The system of the present invention overcomes at least some of the problems, disadvantages and limitations of the prior art described above, and provides a more efficient and accurate means of diagnosing, monitoring and measuring pulmonary congestion based on trans-thoracic impedance values.

The present invention has certain objects. That is, various embodiments of the present invention provide solutions to one or more problems existing in the prior art respecting the pacing of cardiac tissue. Those problems include, without limitation: (a) difficulty in detecting pulmonary congestion in a patient (b) difficulty in quantitatively determining the degree of pulmonary congestion in a patient; (c) difficulty in monitoring the change in pulmonary congestion in a patient over time; (d) need for physician supervision in monitoring pulmonary congestion; (e) difficulty in responding to pulmonary congestion with appropriate therapy.

In comparison to known pacing techniques, various embodiments of the present invention provide one or more of the following advantages: (a) the ability to quantitatively determine the degree of pulmonary congestion in a patient; (b) the ability to monitor pulmonary congestion in a patient over time; (c) the ability to use trans-thoracic impedance values to diagnose pulmonary congestion; (d) the ability to determine trans-thoracic impedance values and exercise level values in a patient; (e) reduced amount of physician supervision in monitoring pulmonary congestion; and (f) the ability to treat pulmonary congestion in a patient based on determined trans-thoracic impedance values.

Some embodiments of the present invention include one or more of the following features: (a) an IPG capable of quantitatively determining the degree of pulmonary congestion in a patient; (b) an IPG capable of using trans-thoracic impedance values to diagnose pulmonary congestion; (c) an IPG capable of monitoring pulmonary congestion; (d) an IPG capable of treating pulmonary congestion; (e) methods of determining the degree of pulmonary congestion in a patient based on impedance values; and (f) methods of diagnosing and treating pulmonary congestion based on impedance values.

At least some embodiments of the present invention involve sensing at least one decrease in a trans-thoracic impedance value from a baseline trans-thoracic impedance value. At least one increase in a heart rate value from a baseline heart rate value is also sensed. Pulmonary congestion is diagnosed if the decrease in the trans-thoracic impedance value corresponding to the increase in the heart rate does not increase after a predetermined interval. The baseline trans-thoracic impedance value, trans-thoracic impedance value, heart rate and predetermined interval may all be determined. In some embodiments of the invention, the trans-thoracic impedance value may be determined by delivering an excitation current pulse between a first electrode and a second electrode and sensing the trans-thoracic impedance between the two electrodes. In some embodiments of the invention, the degree of pulmonary congestion may be determined and appropriate therapy may be delivered.

BRIEF DESCRIPTION OF THE DRAWINGS

The above, and other objects, advantages and features of the present invention will be more readily understood from the following detailed description of the preferred embodiments thereof, when considered in conjunction with the drawings, in which like reference numerals indicate identical structures throughout the several views, and wherein.

DETAILED DESCRIPTION OF THE PRESENTLY PREFERRED EMBODIMENTS

It is to be understood that the terms "IPG" and "IMD", as employed in the specification and claims hereof, means an implantable medical device capable of delivering electrical stimuli to cardiac tissue, and includes within its scope pacemakers, PCDs, ICDs, etc.

Figure 1:
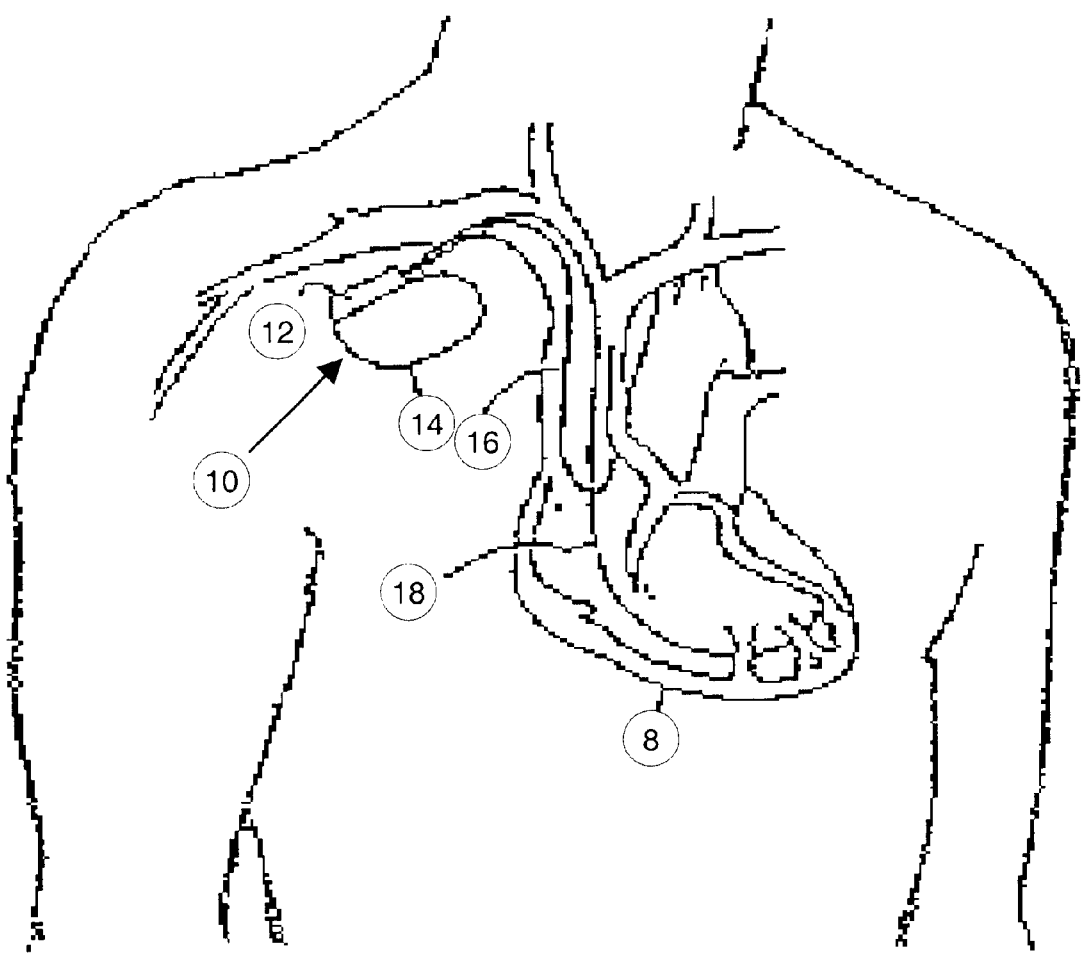
FIG. 1 is a schematic view of an embodiment of an implantable medical device, made in accordance with the present invention.

FIG. 1 is a simplified schematic view of one embodiment of implantable medical device ("IMD") 10 of the present invention. The IMD 10 shown in FIG. 1 is a pacemaker comprising at least one of pacing and sensing leads 16 and 18. Leads 16, 18 may be attached to hermetically sealed enclosure 14 and may be implanted near human or mammalian heart 8. Pacing lead 16 and sensing lead 18 may sense electrical signals attendant to the depolarization and re-polarization of the heart 8, and further provide pacing pulses for causing depolarization of cardiac tissue in the vicinity of the distal ends thereof. Leads 16 and 18 may have unipolar or bipolar electrodes disposed thereon, as is well known in the art. Examples of IMD 10 include implantable cardiac pacemakers disclosed in U.S. Pat. No. 5,158,078 to Bennett et al., U.S. Pat. No. 5,312,453 to Shelton et al. or U.S. Pat. No. 5,144,949 to Olson, all of which are hereby incorporated by reference, each in their respective entireties.

Figure 2:
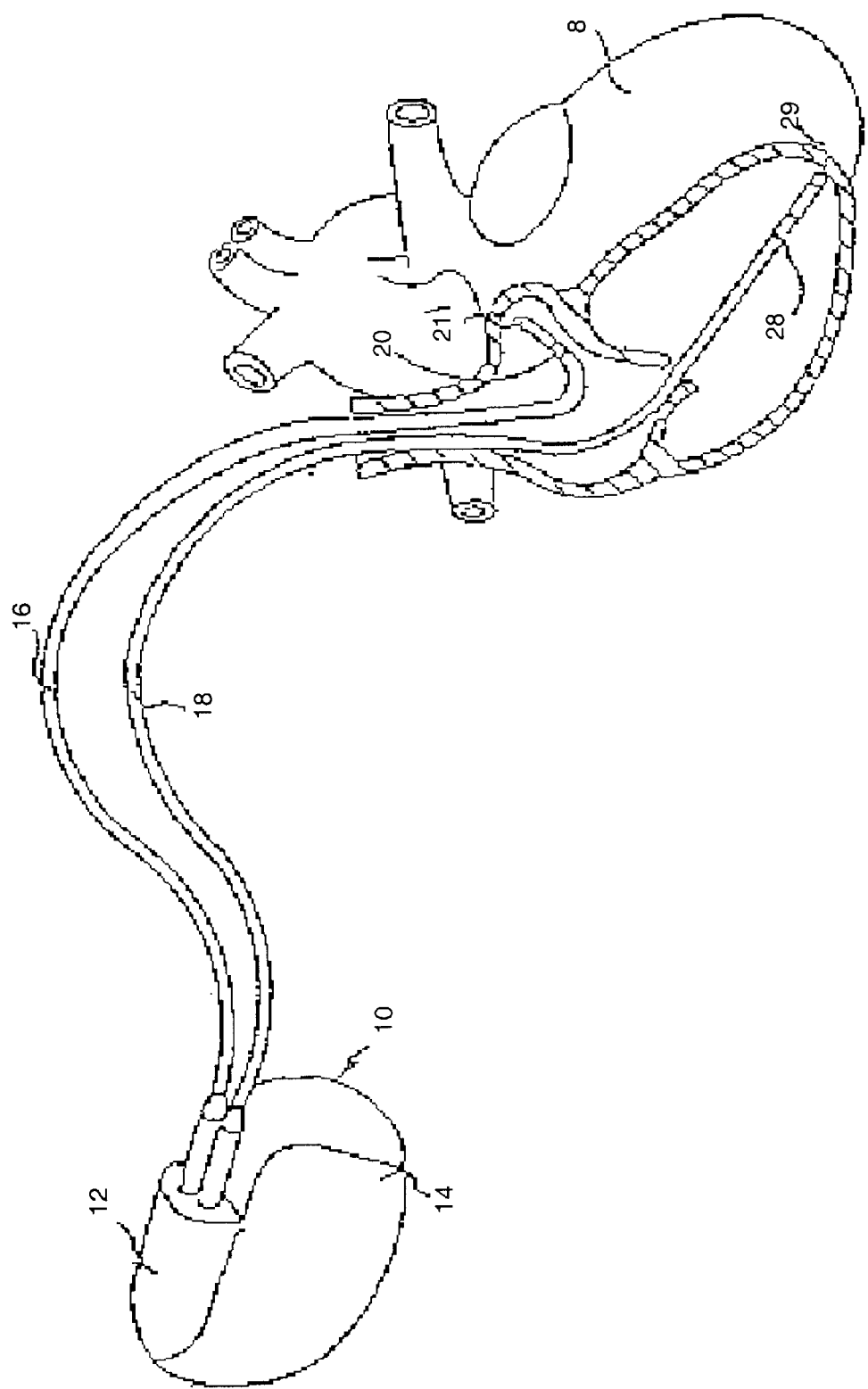
FIG. 2 is another view of the implantable medical device of FIG. 1, made in accordance with the present invention.

FIG. 2 shows connector module 12 and hermetically sealed enclosure 14 of IMD 10 located in and near human or mammalian heart 8. Atrial and ventricular pacing leads 16 and 18 extend from connector header module 12 to the right atrium and ventricle, respectively, of heart 8. Atrial electrodes 20 and 21 disposed at the distal end of atrial pacing lead 16 are located in the right atrium. Ventricular electrodes 28 and 29 at the distal end of ventricular pacing lead 18 are located in the right ventricle.

Figure 3:
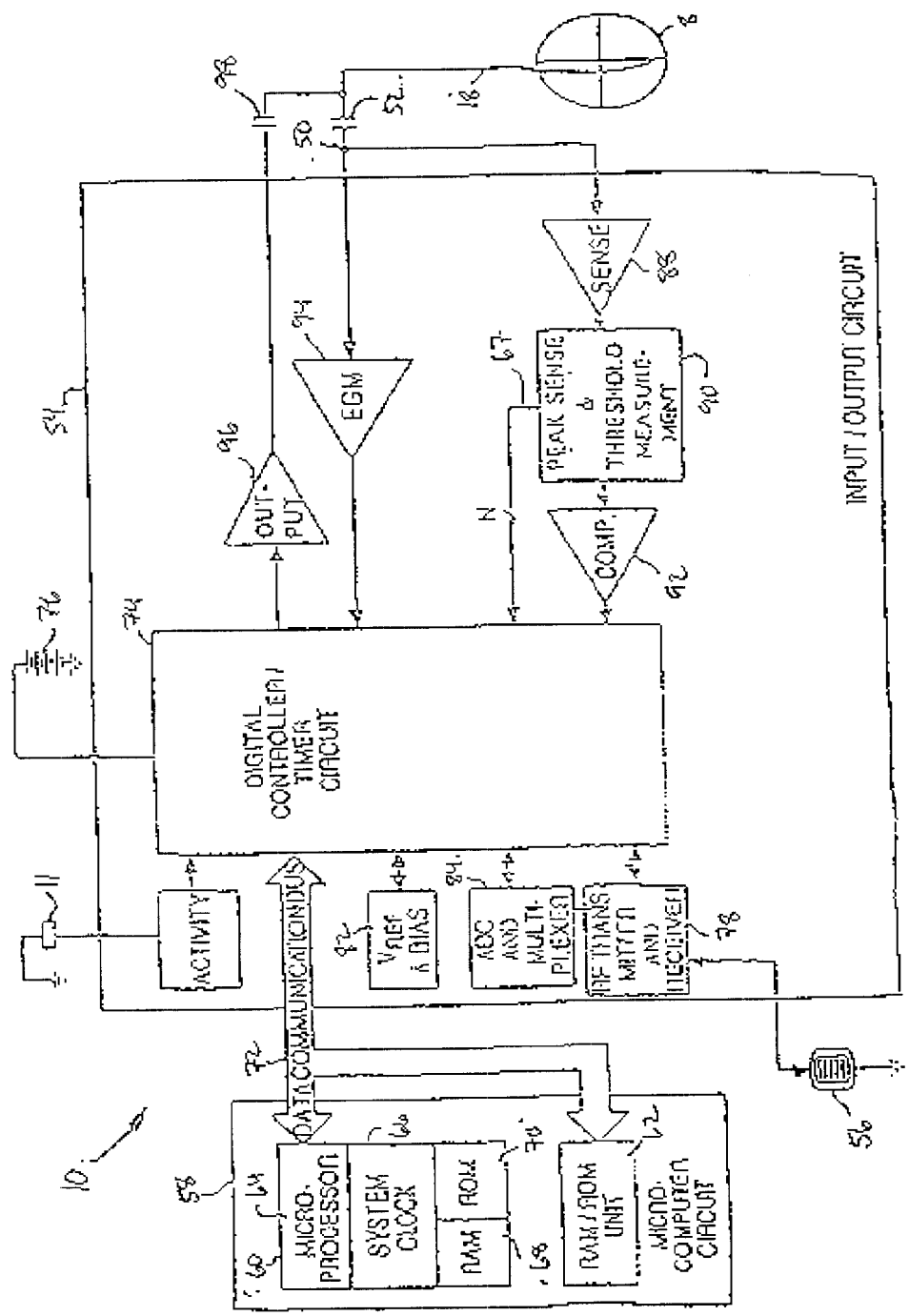
FIG. 3 shows a block diagram illustrating the components of the implantable medical device of FIG. 1, made in accordance with the present invention.

FIG. 3 shows a block diagram illustrating the constituent components of IMD 10 in accordance with one embodiment of the present invention, where IMD 10 is a pacemaker having a microprocessor-based architecture. IMD 10 is shown as including activity sensor 11. Activity sensor 11 may be, for example, an accelerometer based on silicon technology, a piezoceramic accelerometer or an accelerometer bonded to a hybrid circuit located inside enclosure 14. Activity sensor 11 typically (although not necessarily) provides a sensor output that varies as a function of a measured parameter relating to a patient's metabolic requirements. For the sake of convenience, IMD 10 in FIG. 3 is shown with lead 18 only connected thereto; similar circuitry and connections not explicitly shown in FIG. 3 apply to lead 16.

IMD 10 in FIG. 3 is most preferably programmable by means of an external programming unit (not shown in the Figures). One such programmer is the commercially available Medtronic Model 9790 programmer, which is microprocessor-based and provides a series of encoded signals to IMD 10, typically through a programming head which transmits or telemeters radio-frequency (RF) encoded signals to IMD 10. Such a telemetry system is described in U.S. Pat. No. 5,312,453 to Wyborny et al., hereby incorporated by reference in its entirety. The programming methodology disclosed in the '453 patent is identified herein for illustrative purposes only. Any of a number of suitable programming and telemetry methodologies known in the art may be employed so long as the desired information is transmitted to and from the pacemaker.

As shown in FIG. 3, lead 18 is coupled to node 50 in IMD 10 through input capacitor 52. Activity sensor or accelerometer 11 is most preferably attached to a hybrid circuit located inside hermetically sealed enclosure 14 of IMD 10. The output signal provided by activity sensor 11 is coupled to input/output circuit 54. Input/output circuit 54 contains analog circuits for interfacing to heart 8, activity sensor 11, antenna 56 and circuits for the application of stimulating pulses to heart 8. The rate of heart 8 may be controlled by software-implemented algorithms stored in microcomputer circuit 58.

Microcomputer circuit 58 preferably comprises on-board circuit 60 and off-board circuit 62. Circuit 58 may correspond to a microcomputer circuit disclosed in U.S. Pat. No. 5,312,453 to Shelton et al., hereby incorporated by reference in its entirety. On-board circuit 60 preferably includes microprocessor 64, system clock circuit 66 and on-board RAM 68 and ROM 70. Off-board circuit 62 preferably comprises a RAM/ROM unit. On-board circuit 60 and off-board circuit 62 are each coupled by data communication bus 72 to digital controller/timer circuit 74. Microcomputer circuit 58 may comprise a custom integrated circuit device augmented by standard RAM/ROM components.

Electrical components shown in FIG. 3 may be powered by an appropriate implantable battery power source 76 in accordance with common practice in the art. For the sake of clarity, the coupling of battery power to the various components of IMD 10 is not shown in the Figures. Antenna 56 is connected to input/output circuit 54 to permit uplink/downlink telemetry through RF transmitter and receiver telemetry unit 78. By way of example, telemetry unit 78 may correspond to that disclosed in U.S. Pat. No. 4,566,063, issued to Thompson et al. and hereby incorporated by reference in its entirety, or to that disclosed in the above-referenced '453 patent. In one embodiment of the invention, the particular programming and telemetry scheme selected permits the entry and storage of cardiac rate-response parameters. The specific embodiments of antenna 56, input/output circuit 54 and telemetry unit 78 presented herein are shown for illustrative purposes only, and are not intended to limit the scope of the present invention.

Continuing to refer to FIG. 3, $V_{REF}$ and bias circuit 82 most preferably generates stable voltage reference and bias currents for analog circuits included in input/output circuit 54. Analog-to-digital converter (ADC) and multiplexer unit 84 digitizes analog signals and voltages to provide "real-time" telemetry intracardiac signals and battery end-of-life (EOL) replacement functions. Operating commands for controlling the timing of IMD 10 are coupled by data communication bus 72 to digital controller/timer circuit 74, where digital timers and counters establish the overall escape interval of the IMD 10 as well as various refractory, blanking and other timing windows for controlling the operation of peripheral components disposed within input/output circuit 54.

Digital controller/timer circuit 74 is preferably coupled to sensing circuitry, including sense amplifier 88, peak sense and threshold measurement unit 90 and comparator/threshold detector 92. Circuit 74 is further preferably coupled to electrogram (EGM) amplifier 94 for receiving amplified and processed signals sensed by lead 18. Sense amplifier 88 amplifies sensed electrical cardiac signals and provides an amplified signal to peak sense and threshold measurement circuitry 90, which in turn provides an indication of peak sensed voltages and measured sense amplifier threshold voltages on multiple conductor signal path 67 to digital controller/timer circuit 74. An amplified sense amplifier signal is then provided to comparator/threshold detector 92. By way of example, sense amplifier 88 may correspond to that disclosed in U.S. Pat. No. 4,379,459 to Stein, hereby incorporated by reference in its entirety.

The electrogram signal provided by EGM amplifier 94 is employed when IMD 10 is being interrogated by an external programmer to transmit a representation of a cardiac analog electrogram. See, for example, U.S. Pat. No. 4,556,063 to Thompson et al., hereby incorporated by reference herein in its entirety. Output pulse generator 96 provides pacing stimuli to patient's heart 8 through coupling capacitor 98 in response to a pacing trigger signal provided by digital controller/timer circuit 74 each time the escape interval times out, an externally transmitted pacing command is received or in response to other stored commands as is well known in the pacing art. By way of example, output amplifier 96 may correspond generally to an output amplifier disclosed in U.S. Pat. No. 4,476,868 to Thompson, hereby incorporated by reference in its entirety.

The specific embodiments of input amplifier 88, output amplifier 96 and EGM amplifier 94 identified herein are presented for illustrative purposes only, and are not intended to be limiting in respect of the scope of the present invention. The specific embodiments of such circuits may not be critical to practicing some embodiments of the present invention so long as they provide means for generating a stimulating pulse and are capable of providing signals indicative of natural or stimulated contractions of heart 8.

In some preferred embodiments of the present invention, IMD 10 may operate in various non-rate-responsive modes, including, but not limited to, DDD and DDI, modes. In other preferred embodiments of the present invention, IMD 10 may operate in various rate-responsive modes, including, but not limited to, DDDR, DDIR, VVIR, VOOR and VVTR modes. Some embodiments of the present invention are capable of operating in both non-rate-responsive and rate responsive modes. Moreover, in various embodiments of the present invention IMD 10 may be programmably configured to operate so that it varies the rate at which it delivers stimulating pulses to heart 8 only in response to one or more selected sensor outputs being generated. Numerous pacemaker features and functions not explicitly mentioned herein may be incorporated into IMD 10 while remaining within the scope of the present invention.

The present invention is not limited in scope to single-sensor or dual-sensor pacemakers, and is further not limited to IMDs comprising activity or pressure sensors only. Nor is the present invention limited in scope to single-chamber pacemakers, single-chamber leads for pacemakers or single-sensor or dual-sensor leads for pacemakers. Thus, various embodiments of the present invention may be practiced in conjunction with more than two leads or with multiple-chamber pacemakers, for example. At least some embodiments of the present invention may be applied equally well in the contexts of single-, dual-, triple- or quadruple-chamber pacemakers or other types of IMDs. See, for example, U.S. Pat. No. 5,800,465 to Thompson et al., hereby incorporated by reference herein in its entirety, as are all U.S. Patents referenced therein.

IMD 10 may also be a pacemaker-cardioverter-defibrillator ("PCD") corresponding to any of numerous commercially available implantable PCDs. Various embodiments of the present invention may be practiced in conjunction with PCDs such as those disclosed in U.S. Pat. No. 5,545,186 to Olson et al., U.S. Pat. No. 5,354,316 to Keimel, U.S. Pat. No. 5,314,430 to Bardy, U.S. Pat. No. 5,131,388 to Pless and U.S. Pat. No. 4,821,723 to Baker et al., all of which are hereby incorporated by reference, each in their respective entireties.

Figure 4:
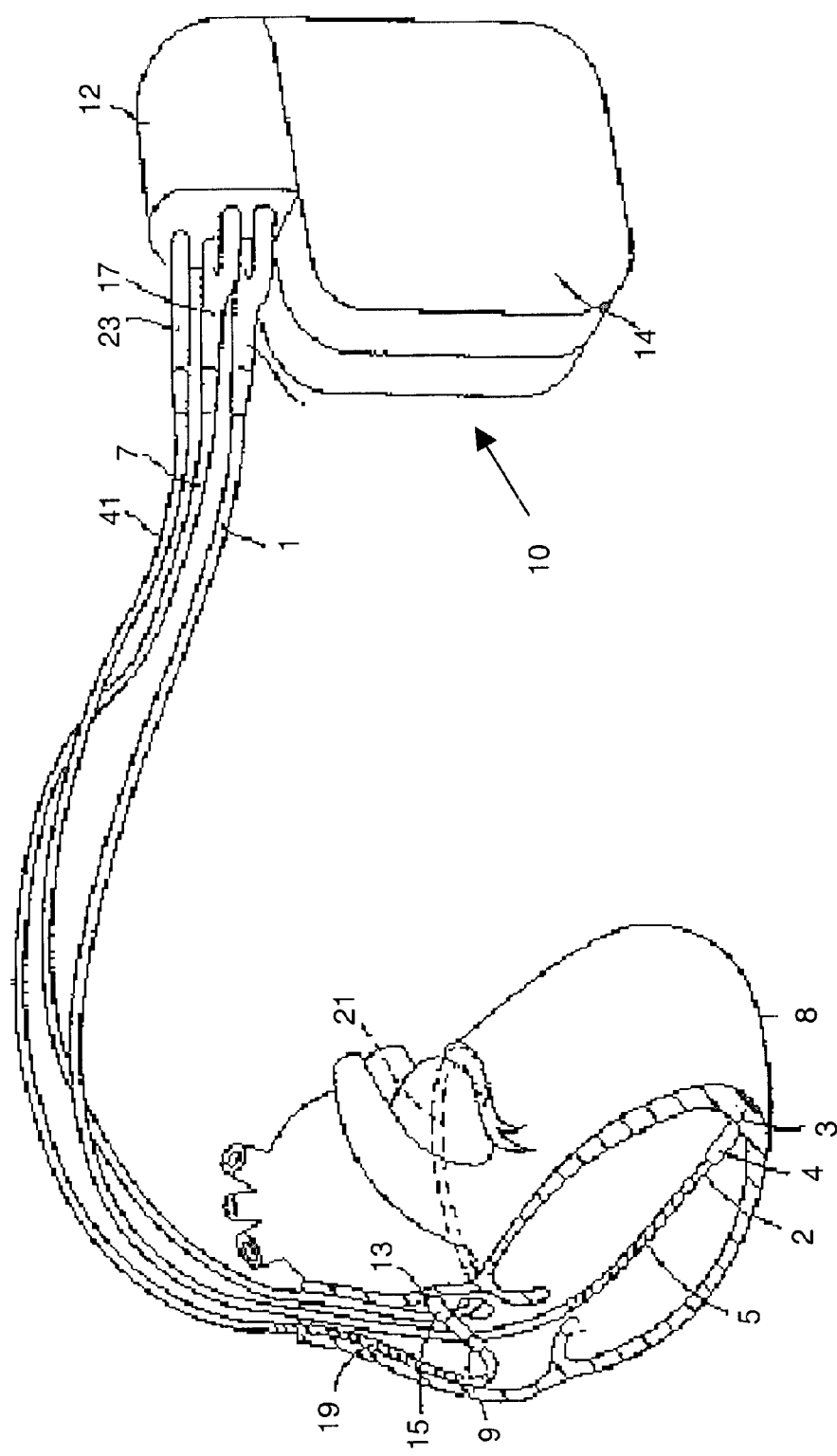
FIG. 4 illustrates another embodiment of an implantable medical device, made in accordance with the present invention.
Figure 5:
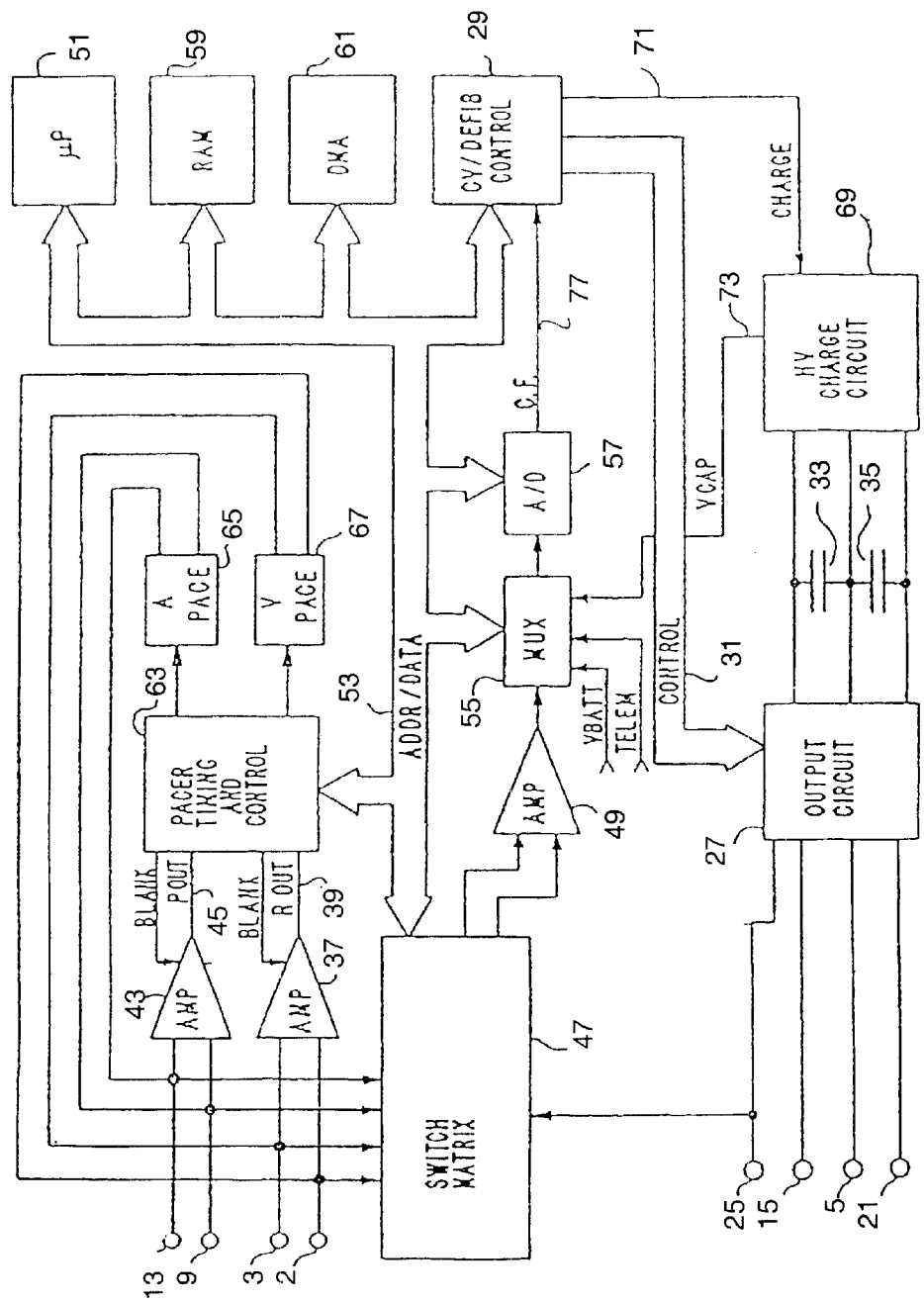
FIG. 5 illustrates a block diagram of the embodiment of FIG. 4, made in accordance with the present invention.

FIGS. 4 and 5 illustrate one embodiment of IMD 10 and a corresponding lead set of the present invention, where IMD 10 is a PCD. In FIG. 4, the ventricular lead takes the form of leads disclosed in the '838 and '430 patents, and includes an elongated insulative lead body 1 carrying three concentric coiled conductors separated from one another by tubular insulative sheaths. Located adjacent the distal end of lead 1 are ring electrode 2, extendable helix electrode 3 mounted retractably within insulative electrode head 4 and elongated coil electrode 5. Each of the electrodes is coupled to one of the coiled conductors within lead body 1. Electrodes 2 and 3 are employed for cardiac pacing and for sensing ventricular depolarizations. At the proximal end of the lead is bifurcated connector 6, which carries three electrical connectors, each coupled to one of the coiled conductors. Defibrillation electrode 5 may be fabricated from platinum, platinum alloy or other materials known to be usable in implantable defibrillation electrodes and may be about 5 cm in length.

The atrial/SVC lead shown in FIG. 4 includes elongated insulative lead body 7 carrying three concentric coiled conductors separated from one another by tubular insulative sheaths corresponding to the structure of the ventricular lead. Located adjacent the J-shaped distal end of the lead are ring electrode 9 and extendable helix electrode 13 mounted retractably within an insulative electrode head 15. Each of the electrodes is coupled to one of the coiled conductors within lead body 7. Electrodes 13 and 9 are employed for atrial pacing and for sensing atrial depolarizations. Elongated coil electrode 19 is provided proximal to electrode 9 and coupled to the third conductor within lead body 7. Electrode 19 preferably is 10 cm in length or greater and is configured to extend from the SVC toward the tricuspid valve. In one embodiment of the present invention, approximately 5 cm of the right atrium/SVC electrode is located in the right atrium with the remaining 5 cm located in the SVC. At the proximal end of the lead is bifurcated connector 17, which carries three electrical connectors, each coupled to one of the coiled conductors.

The coronary sinus lead shown in FIG. 4 assumes the form of a coronary sinus lead disclosed in the above cited '838 patent, and includes elongated insulative lead body 41 carrying one coiled conductor coupled to an elongated coiled defibrillation electrode 21. Electrode 21, illustrated in broken outline in FIG. 4, is located within the coronary sinus and the great vein of the heart. At the proximal end of the lead is connector plug 23 carrying an electrical connector coupled to the coiled conductor. The coronary sinus/great vein electrode 41 may be about 5 cm in length.

Implantable PCD 10 is shown in FIG. 4 in combination with leads 1, 7 and 41, and lead connector assemblies 23, 17 and 6 inserted into connector Block 12. Optionally, insulation of the outward facing portion of housing 14 of PCD 10 may be provided using a plastic coating such as parylene or silicone rubber, as is employed in some unipolar cardiac pacemakers. The outward facing portion, however, may be left uninsulated or some other division between insulated and uninsulated portions may be employed. The uninsulated portion of housing 14 serves as a subcutaneous defibrillation electrode to defibrillate either the atria or ventricles. Lead configurations other that those shown in FIG. 4 may be practiced in conjunction with the present invention, such as those shown in U.S. Pat. No. 5,690,686 to Min et al., hereby incorporated by reference in its entirety.

FIG. 5 is a functional schematic diagram of one embodiment of implantable PCD 10 of the present invention. This diagram should be taken as exemplary of the type of device in which various embodiments of the present invention may be embodied, and not as limiting, as it is believed that the invention may be practiced in a wide variety of device implementations, including cardioverter and defibrillators which do not provide anti-tachycardia pacing therapies.

PCD 10 is provided with an electrode system. If the electrode configuration of FIG. 4 is employed, the correspondence to the illustrated electrodes is as follows. Electrode 25 in FIG. 5 includes the uninsulated portion of the housing of PCD 10. Electrodes 25, 15, 21 and 5 are coupled to high voltage output circuit 27, which includes high voltage switches controlled by CV/defib control logic 29 via control bus 31. Switches disposed within circuit 27 determine which electrodes are employed and which electrodes are coupled to the positive and negative terminals of the capacitor bank (which includes capacitors 33 and 35) during delivery of defibrillation pulses.

Electrodes 2 and 3 are located on or in the ventricle and are coupled to the R-wave amplifier 37, which preferably takes the form of an automatic gain controlled amplifier providing an adjustable sensing threshold as a function of the measured R-wave amplitude. A signal is generated on R-out line 39 whenever the signal sensed between electrodes 2 and 3 exceeds the present sensing threshold.

Electrodes 9 and 13 are located on or in the atrium and are coupled to the P-wave amplifier 43, which preferably also takes the form of an automatic gain controlled amplifier providing an adjustable sensing threshold as a function of the measured P-wave amplitude. A signal is generated on P-out line 45 whenever the signal sensed between electrodes 9 and 13 exceeds the present sensing threshold. The general operation of R-wave and P-wave amplifiers 37 and 43 may correspond to that disclosed in U.S. Pat. No. 5,117,824, by Keimel et al., issued Jun. 2, 1992, for "An Apparatus for Monitoring Electrical Physiologic Signals," hereby incorporated by reference in its entirety.

Switch matrix 47 is used to select which of the available electrodes are coupled to wide band (0.5–200 Hz) amplifier 49 for use in digital signal analysis. Selection of electrodes is controlled by the microprocessor 51 via data/address bus 53, which selections may be varied as desired. Signals from the electrodes selected for coupling to bandpass amplifier 49 are provided to multiplexer 55, and thereafter converted to multi-bit digital signals by A/D converter 57, for storage in RAM 59 under control of direct memory access circuit 61. Microprocessor 51 may employ digital signal analysis techniques to characterize the digitized signals stored in RAM 59 to recognize and classify the patient's heart rhythm employing any of the numerous signal-processing methodologies known to the art.

The remainder of the circuitry is dedicated to the provision of cardiac pacing, cardioversion and defibrillation therapies, and, for purposes of the present invention, may correspond to circuitry known to those skilled in the art. The following exemplary apparatus is disclosed for accomplishing pacing, cardioversion and defibrillation functions. Pacer timing/control circuitry 63 preferably includes programmable digital counters which control the basic time intervals associated with DDD, VVI, DVI, VDD, AAI, DDI and other modes of single and dual chamber pacing well known to the art. Circuitry 63 also preferably controls escape intervals associated with anti-tachyarrhythmia pacing in both the atrium and the ventricle, employing any anti-tachyarrhythmia pacing therapies known to the art.

Intervals defined by pacing circuitry 63 include atrial and ventricular pacing escape intervals, the refractory periods during which sensed P-waves and R-waves are ineffective to restart timing of the escape intervals and the pulse widths of the pacing pulses. The durations of these intervals are determined by microprocessor 51, in response to stored data in memory 59 and are communicated to pacing circuitry 63 via address/data bus 53. Pacer circuitry 63 also determines the amplitude of the cardiac pacing pulses under control of microprocessor 51.

During pacing, escape interval counters within pacer timing/control circuitry 63 are reset upon sensing of R-waves and P-waves as indicated by signals on lines 39 and 45, and in accordance with the selected mode of pacing on time-out trigger generation of pacing pulses by pacer output circuitry 65 and 67, which are coupled to electrodes 9, 13, 2 and 3. Escape interval counters are also reset on the generation of pacing pulses and thereby control the basic timing of cardiac pacing functions, including anti-tachyarrhythmia pacing. The durations of the intervals defined by escape interval timers are determined by microprocessor 51 via data/address bus 53. The value of the count present in the escape interval counters when reset by sensed R-waves and P-waves may be used to measure the durations of R-R intervals, P-P intervals, P-R intervals and R-P intervals, which measurements are stored in memory 59 and used to detect the presence of tachyarrhythmias.

Microprocessor 51 most preferably operates as an interrupt driven device, and is responsive to interrupts from pacer timing/control circuitry 63 corresponding to the occurrence of sensed P-waves and R-waves and corresponding to the generation of cardiac pacing pulses. Those interrupts are provided via data/address bus 53. Any necessary mathematical calculations to be performed by microprocessor 51 and any updating of the values or intervals controlled by pacer timing/control circuitry 63 take place following such interrupts.

Detection of atrial or ventricular tachyarrhythmias, as employed in the present invention, may correspond to any of the various tachyarrhythmia detection algorithms presently known in the art. For example, the presence of an atrial or ventricular tachyarrhythmia may be confirmed by detecting a sustained series of short R-R or P-P intervals of an average rate indicative of tachyarrhythmia or an unbroken series of short R-R or P-P intervals. The suddenness of onset of the detected high rates, the stability of the high rates, and a number of other factors known in the art may also be measured at this time. Appropriate ventricular tachyarrhythmia detection methodologies measuring such factors are described in U.S. Pat. No. 4,726,380 issued to Vollmann, U.S. Pat. No. 4,880,005, issued to Pless et al. and U.S. Pat. No. 4,830,006, issued to Haluska et al., all hereby incorporated by reference, each in their respective entirety. An additional set of tachycardia recognition methodologies is disclosed in the article "Onset and Stability for Ventricular Tachyarrhythmia Detection in an Implantable Pacer-Cardioverter-Defibrillator" by Olson et al., published in Computers in Cardiology, Oct. 7–10, 1986, *IEEE Computer Society Press*, pp. 167–170, also hereby incorporated by reference in its entirety. Atrial fibrillation detection methodologies are disclosed in published PCT Application Serial No. US92/02829, Publication No. WO92/18198, by Adams et al., and in the article "Automatic Tachycardia Recognition", by Arzbaecher et al., published in PACE, May–June, 1984, pp. 541–547, both of which are hereby incorporated by reference in their entireties.

In the event an atrial or ventricular tachyarrhythmia is detected and an anti-tachyarrhythmia pacing regimen is desired, appropriate timing intervals for controlling generation of anti-tachyarrhythmia pacing therapies are loaded from microprocessor 51 into the pacer timing and control circuitry 63, to control the operation of the escape interval counters therein and to define refractory periods during which detection of R-waves and P-waves is ineffective to restart the escape interval counters.

Alternatively, circuitry for controlling the timing and generation of anti-tachycardia pacing pulses as described in U.S. Pat. No. 4,577,633, issued to Berkovits et al. on Mar. 25, 1986, U.S. Pat. No. 4,880,005, issued to Pless et al. on Nov. 14, 1989, U.S. Pat. No. 4,726,380, issued to Vollmann et al. on Feb. 23, 1988 and U.S. Pat. No. 4,587,970, issued to Holley et al. on May 13, 1986, all of which are hereby incorporated by reference in their entireties, may also be employed.

In the event that the generation of a cardioversion or defibrillation pulse is required, microprocessor 51 may employ an escape interval counter to control timing of such cardioversion and defibrillation pulses, as well as the associated refractory periods. In response to the detection of atrial or ventricular fibrillation or tachyarrhythmia requiring a cardioversion pulse, microprocessor 51 activates cardioversion/defibrillation control circuitry 29, which initiates charging of the high voltage capacitors 33 and 35 via charging circuit 69, under the control of high voltage charging control line 71. The voltage on the high voltage capacitors is monitored via VCAP line 73, which is passed through multiplexer 55 and in response to reaching a predetermined value set by microprocessor 51, results in generation of a logic signal on Cap Full (CF) line 77 to terminate charging. Thereafter, timing of the delivery of the defibrillation or cardioversion pulse is controlled by pacer timing/control circuitry 63. Following delivery of the fibrillation or tachycardia therapy, microprocessor 51 returns the device to a cardiac pacing mode and awaits the next successive interrupt due to pacing or the occurrence of a sensed atrial or ventricular depolarization.

Several embodiments of appropriate systems for the delivery and synchronization of ventricular cardioversion and defibrillation pulses and for controlling the timing functions related to them are disclosed in U.S. Pat. No. 5,188,105 to Keimel, U.S. Pat. No. 5,269,298 to Adams et al. and U.S. Pat. No. 4,316,472 to Mirowski et al., all of which are hereby incorporated by reference, each in its respective entirety. Any known cardioversion or defibrillation pulse control circuitry is believed to be usable in conjunction with various embodiments of the present invention, however. For example, circuitry controlling the timing and generation of cardioversion and defibrillation pulses such as that disclosed in U.S. Pat. No. 4,384,585 to Zipes, U.S. Pat. No. 4,949,719 to Pless et al., or U.S. Pat. No. 4,375,817 to Engle et al., all of which are hereby incorporated by reference in their entireties, may also be employed.

Continuing to refer to FIG. 5, delivery of cardioversion or defibrillation pulses may be accomplished by output circuit 27 under the control of control circuitry 29 via control bus 31. Output circuit 27 determines whether a monophasic or biphasic pulse is delivered, the polarity of the electrodes and which electrodes are involved in delivery of the pulse. Output circuit 27 also includes high voltage switches, which control whether electrodes are coupled together during delivery of the pulse. Alternatively, electrodes intended to be coupled together during the pulse may simply be permanently coupled to one another, either exterior to or within the interior of the device housing, and polarity may similarly be pre-set, as in current implantable defibrillators. An example of output circuitry for delivery of biphasic pulse regimens to multiple electrode systems may be found in U.S. Pat. No. 4,953,551, issued to Mehra, and in U.S. Pat. No. 4,727,877, both of which are hereby incorporated by reference in their entireties.

An example of circuitry that may be used to control delivery of monophasic pulses is disclosed in U.S. Pat. No. 5,163,427 to Keimel, also hereby incorporated by reference in its entirety. Output control circuitry similar to that disclosed in the '551 patent or in U.S. Pat. No. 4,800,883 to Winstrom, which is hereby incorporated by reference in its entirety, may also be used in conjunction with various embodiments of the present invention to deliver biphasic pulses.

Alternatively, IMD 10 may be an implantable nerve stimulator or muscle stimulator, such as that disclosed in U.S. Pat. No. 5,199,428 to Obel et al., U.S. Pat. No. 5,207,218 to Carpentier et al. or U.S. Pat. No. 5,330,507 to Schwartz, or an implantable monitoring device such as that disclosed in U.S. Pat. No. 5,331,966 issued to Bennet et al., all of which are hereby incorporated by reference, each in their respective entireties. The present invention is believed to find wide application to any form of implantable electrical device for use in conjunction with electrical leads.

Alternatively, IMD 10 may be an implantable monitoring device, which does not include electrodes in either the atrium or the ventricle. Such an implantable monitoring device may be, for example, an injectable monitor capable of impedance sensing. For example, IMD 10 may be an impedance monitor that includes an impedance sensor. The impedance sensor may be, for example, an accelerometer based on silicon technology, a piezoceramic accelerometer or an accelerometer bonded to a hybrid circuit located inside enclosure 14. The impedance sensor typically (although not necessarily) provides a sensor output that varies as a function of a measured parameter relating to a patient's metabolic requirements, such as, for example, a patient's trans-thoracic impedance values. In one embodiment of the invention, IMD 10 may include an additional lead for creating a large enough dipole to measure pulmonary congestion. Such a lead may be, for example, one or more of leads 16, 18 or any suitable lead as described above. In another embodiment of the invention, IMD 10 may include an activity sensor 11 which may be used to monitor the heart's electrical activity. It is contemplated that impedance sensor and activity sensor 11 may be the same sensor.

Whether or not it is coupled with one or more leads, the impedance sensor may provide a series of encoded signals related to IMD 10, typically through a programming head that transmits or telemeters radio-frequency (RF) encoded signals to IMD 10. Such a telemetry system is described in U.S. Pat. No. 5,312,453 to Wyborny et al., hereby incorporated by reference in its entirety. The programming methodology disclosed in the '453 patent is identified herein for illustrative purposes only. Any of a number of suitable programming and telemetry methodologies known in the art may be employed so long as the desired information is transmitted to and from the implantable monitoring device.

IMD 10 may further include input/output circuit 54 which may contain analog circuits for interfacing to heart 8, activity sensor 11, impedance sensor and antenna 56. In one embodiment of the, invention, IMD 10 may further comprise on-board circuit 60 and off-board circuit 62. Circuit 58 may correspond to a microcomputer circuit disclosed in U.S. Pat. No. 5,312,453 to Shelton et al., hereby incorporated by reference in its entirety. On-board circuit 60 preferably includes microprocessor 64, system clock circuit 66 and on-board RAM 68 and ROM 70. Off-board circuit 62 preferably comprises a RAM/ROM unit. On-board circuit 60 and off-board circuit 62 are each coupled by data communication bus 72 to digital controller/timer circuit 74. Microcomputer circuit 58 may comprise a custom integrated circuit device augmented by standard RAM/ROM components.

Electrical components of IMD 10 may be powered by an appropriate implantable battery power source 76 in accordance with common practice in the art.

IMD 10 may also include digital controller/timer circuit 74 which may be coupled to sensing circuitry, including sense amplifier 88, peak sense and threshold measurement unit 90 and comparator/threshold detector 92. Sense amplifier 88 amplifies sensed impedance signals and provides an amplified signal to peak sense and threshold measurement circuitry 90, which in turn provides an indication of peak sensed voltages and measured sense amplifier threshold voltages on multiple conductor signal path 67 to digital controller/timer circuit 74. An amplified sense amplifier signal is then provided to comparator/threshold detector 92. By way of example, sense amplifier 88 may correspond to that disclosed in U.S. Pat. No. 4,379,459 to Stein, hereby incorporated by reference in its entirety.

In one embodiment of the invention, IMD 10 is injectable.

The present invention is based on the physiology of the pulmonary anatomy, and particularly on the fact that the pulmonary circulation is closely related to the cardiac condition. Thus, pulmonary circulation may be used as an indication of cardiac condition, and ultimately heart failure. Alternatively, measurements of cardiac condition may be correlated with pulmonary congestion.

In particular, cardiac condition is closely related to right atrial pressure. This is seen in the Frank-Starling law, which describes the relationship between cardiac output and right atrial pressure as a curvilinear function. A sustained increase of hydrostatic pressure in the pulmonary veins, however, indicates a failure of the Frank-Starling Law in the left ventricle.

In patients, increase of hydrostatic pressure in the pulmonary veins often leads to pulmonary edema in the lower lobes of the lungs. Moreover, as the failure becomes more acute, the pulmonary edema may become more widespread, progressing from the lower lobes of the lungs to the upper lobes.

The present invention uses this physiology to indicate pulmonary congestion. In particular, the present invention senses the trans-thoracic impedance, which is dependent on the blood or fluid content of the lungs, to assist in the detection and quantification of pulmonary edema and thus pulmonary congestion.

The present invention may also use other values to quantify pulmonary edema in addition to trans-thoracic impedance values. Trans-thoracic impedance is affected by the level of exercise of the patient. In a healthy patient who has just begun exercising, the pulmonary veins are filled up; therefore trans-thoracic impedance will drop for a short period. In a healthy patient, the Frank-Starling Law will be unaffected; the trans-thoracic impedance will quickly thereafter return back up towards its baseline value and the left ventricular flow out of the lungs will increase. The trans-thoracic impedance will rise briefly when the patient terminates exercise before returning to its baseline value.

In a patient with mild congestive heart failure, however, pulmonary congestion is often present while the patient is beginning to exercise. Trans-thoracic impedance will decrease and remain at a lower level throughout the exercise. At the end of exercise, trans-thoracic impedance will again return to its baseline value. Impedance will remain at its decreased position in congestive heart failure patients due to the heart's failing Frank-Starling mechanism. That is, the heart's inadequate ability to pump blood and thus control the hydrostatic pressure in the arteries and veins of the lungs will keep impedance at its decreased position.

In a patient with moderate congestive heart failure, trans-thoracic impedance may continue to decrease throughout exercise because of the development of edema. Trans-thoracic impedance in this case may only return to its initial baseline value reading sometime after the patient has stopped exercising.

In a patient with severe congestive heart failure, impedance may remain low due to the persistence of pulmonary edema or congestion. Trans-thoracic impedance in this case may not return to its initial baseline value reading or may do so well after the time the patient has stopped exercising.

Based on these general guidelines, which are for illustrative purposes and are not intended to limit the scope of the present invention, a method of diagnosing pulmonary congestion in a mammalian heart is provided. A decrease in trans-thoracic impedance values may be sensed in heart 8. An increase may also be sensed in a heart rate of heart 8. In one embodiment of the invention, this increase in heart rate may be the result of exercise. Finally, pulmonary congestion may be diagnosed if the decrease in the trans-thoracic impedance as a result of the increase in the heart rate does not resolve after a predetermined period of time. Although the present invention is described in the context of an implantable pulse generator system, this example only serves to illustrate various aspects of the present invention. It is to be understood that the present invention may be practiced in conjunction with various types of implantable devices, including, for example defibrillators, cardioverters, heart monitors, drug delivery systems, injectable monitors, implantable monitors and the like.

Figure 6:
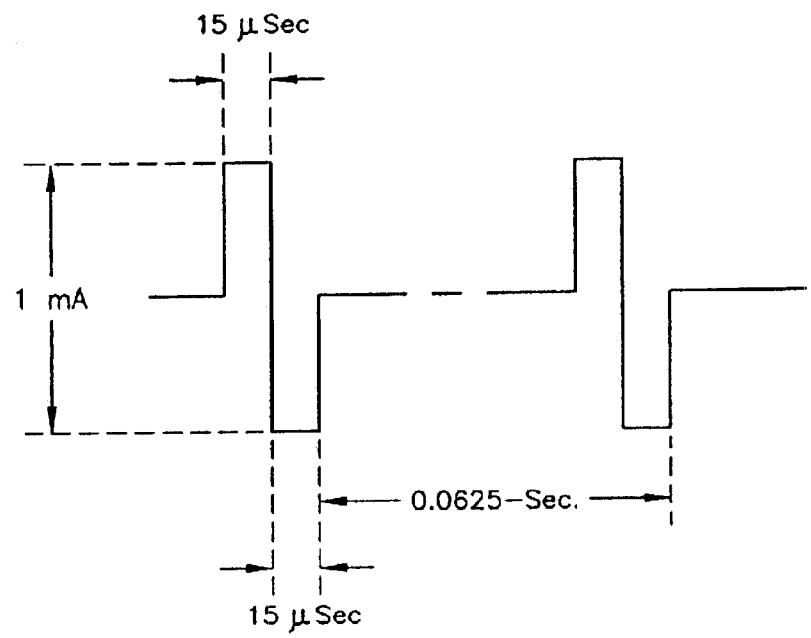
FIG. 6 illustrates an excitation current pulse delivered by the impedance circuitry of the implantable medical device of the present invention.

FIG. 6 illustrates an excitation current pulse delivered by the impedance circuitry of IMD 10, as shown and described above in FIG. 5. A biphasic excitation pulse offers a number of advantages over a monophasic pulse. For example, the peak amplitude of the excitation pulse may be minimized, given the overall energy content of the pulse. Electrode polarization may be canceled. The direct current may be balanced, which helps to avoid long-term lead metal-ion oxidation. As shown in FIG. 6, each phase of the biphasic pulse lasts for approximately 15 ms, and the pulses themselves are transmitted once every 0.0625 s (i.e., at a rate of 16 Hz). Alternatively, a monophasic pulse may be used.

In one embodiment, the impedance values may be measured over a predetermined period of time and an average value may be determined. Thus, the pulse described in FIG. 6 may be delivered one or more times over a predetermined period of time. For example, this period of time may range from 10 to 100, 30 to 80 and 50 to 70 seconds. In one embodiment of the invention, the impedance values are measured over a period of 60 seconds. Alternatively, the impedance values may be measured over a predetermined number of breathing cycles and an average value may be determined. For example, the values may be measured over a range of 1 to 5 or 2 to 4 breathing cycles. In one embodiment of the invention, the impedance values are measured over 3 breathing cycles.

The sensed impedance values may also be filtered. In one embodiment of the invention, coughing is detected. A coughing value may be determined. This coughing value may be used to adjust the impedance value for coughing by the patient. Alternatively, the coughing value may be used as another input for quantifying and assessing the pulmonary congestion, as well as the efficiency of a particular therapy. In one embodiment of the invention, an adjustment may be made to the coughing value based on a factor of induced coughing. That is, some patients with pulmonary congestion may be taking ACE inhibitors, which sometimes induce coughing. Thus, whether or not the coughing value is induced, for example by an ACE inhibitor or other drug, may be taken into consideration as part of the coughing value. The coughing value may be determined, for example, by analyzing the higher frequency components of the impedance signals. Coughs may also be detected through a piezoelectric crystal on the device housing or through a lead-based accelerometer on a lead.

Figure 7A:
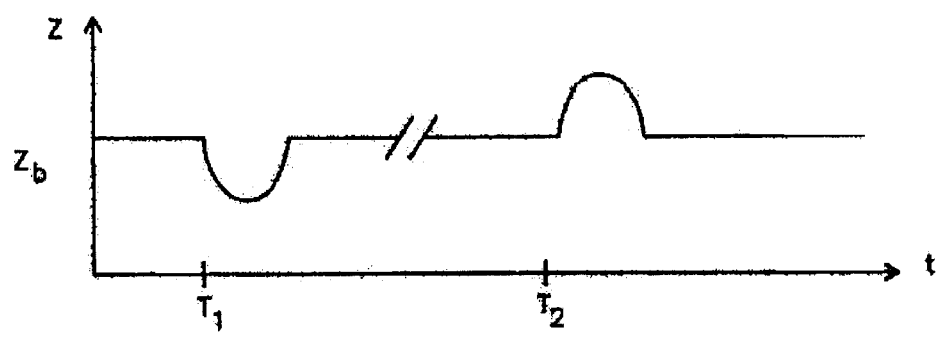
FIGS. 7a, 7b and 7c depict the change in trans-thoracic impedance in three different patients.

FIGS. 7a, b and c depict the change in trans-thoracic impedance in three different patients.

FIG. 7a depicts the change in impedance in a first patient over the time interval between the commencement and the termination of exercise. The change in impedance shown in FIG. 7a may be, for example, that of a patient with a healthy heart. As seen, at time T1, the commencement of exercise, the sensed trans-thoracic impedance will decrease. The trans-thoracic impedance decrease is due to an initial increase in the amount of fluid in the thoracic cavity, especially in and around the lungs. If the patient has a healthy heart, the initial decrease in trans-thoracic impedance will be compensated for by heart 8 and will shortly thereafter return to its baseline value, shown in FIG. 7a as $Z_b$. Similarly at time T2, when the patient terminates exercise, the trans-thoracic impedance begins to increase as fluid initially drains from the lungs to the lower extremities. Again, if the patient has a healthy heart, the initial increase in trans-thoracic impedance will be compensated for by heart 8, and will shortly thereafter return back to its baseline value.

Figure 7B:
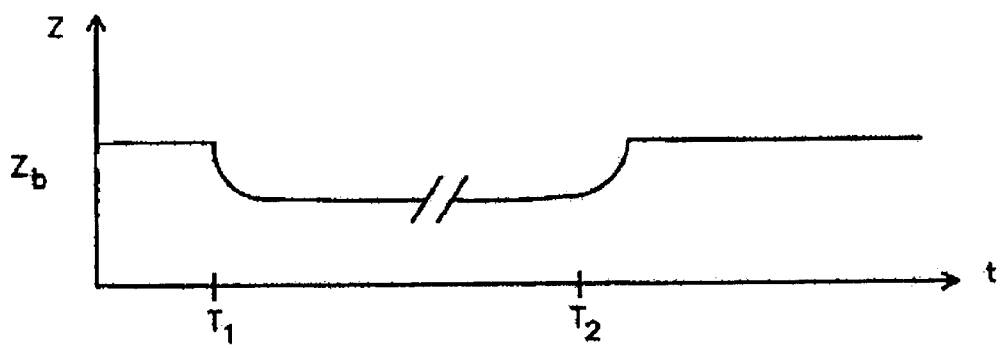

FIG. 7b depicts the change in impedance in another patient over the time interval between the commencement and the termination of exercise. The change in impedance shown in FIG. 7b may be, for example, that of a patient with a mild degree of pulmonary congestion. Similar to a healthy subject, at time T1 when the patient has commenced exercise, the sensed trans-thoracic impedance will decrease. Because the patient has a mild degree of pulmonary congestion, however, heart 8 is incapable of immediately returning the fluid imbalance in the thoracic cavity to its baseline condition. As a result, pulmonary congestion occurs and the initial decrease in trans-thoracic impedance cannot by compensated for by heart 8. Thus, as is shown, over time, the trans-thoracic impedance remains at a depressed level until the patient terminates exercise at time T2.

Figure 7C:
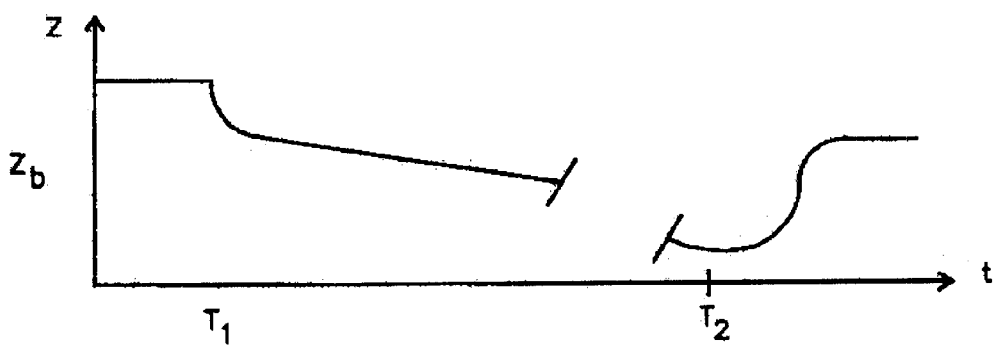

FIG. 7c depicts the change in impedance in a third patient over the time interval between the commencement and the termination of exercise. The change in impedance shown in FIG. 7c may be, for example, that of a patient with a severe degree of pulmonary congestion. As is shown in FIG. 7c, in this patient, the initial sensed trans-thoracic impedance decrease does not reach a constant value, but rather continues to drop throughout the period of exercise. This indicates a continuous increase of fluid and results in pulmonary edema until the patient terminates exercise at time T2. As seen in FIG. 7c, the return to baseline value $Z_b$ may not occur until well after the patient has terminated exercise.

Figure 8:
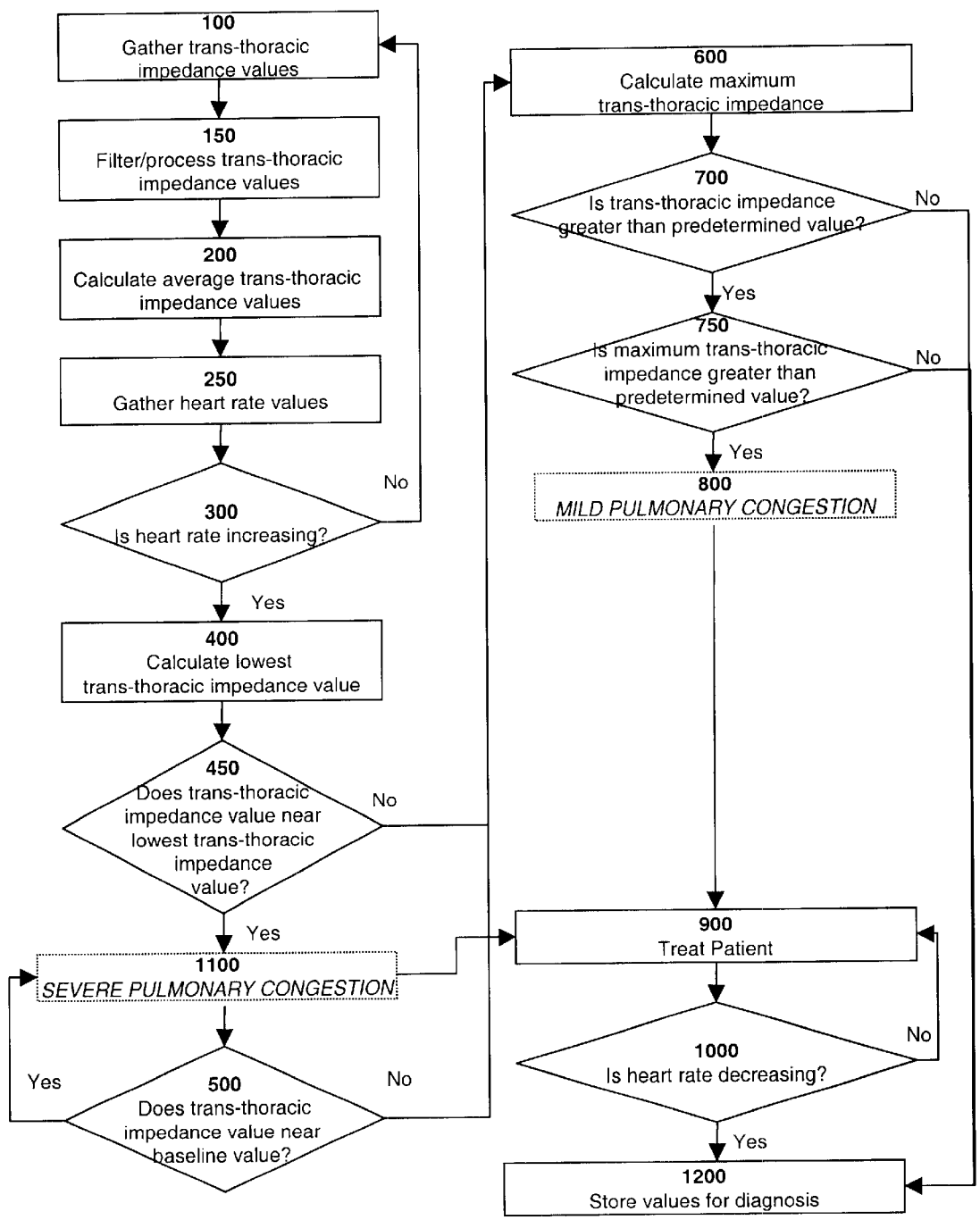
FIG. 8 illustrates a flow chart of a routine of a method of diagnosing pulmonary congestion in a mammalian heart.

FIG. 8 is a flow chart illustrating a method of diagnosing pulmonary congestion in a mammalian heart in accordance with the present invention. As seen in FIG. 8, the present invention may be used to measure one or more parameters indicative of pulmonary congestion. The parameters measured may include the trans-thoracic impedance of the patient and any changes in trans-thoracic impedance subsequent to an increase in exercise. As discussed above, the method of the present invention may be performed under the control of any appropriate computer algorithm stored in a memory or a portion of a memory of microcomputer 58 in IMD 10. Such a computer algorithm may be any program capable of being stored in an electronic medium such as, by way of example only, RAM 68 or ROM 70 of IMD 10, where the contents of RAM 68 and ROM 70 may be accessed and consequently executed by microprocessor 64/microcomputer 58.

As is shown in FIG. 8, at Block 800, IMD 10 may measure multiple trans-thoracic impedance values. The multiple trans-thoracic impedance values may be measured by transmitting a small (threshold) excitation current to heart 8 via electrodes 2, 3, 9, 13, and measuring the resulting voltage difference. The resulting voltage difference is dependent upon the impedance found in the tissues disposed between electrodes 2, 3, 9, 13. Alternatively, the impedance values may be measured by a simple monitor as described above, with or without the use of electrodes.

The impedance measurements taken here may represent the impedance changes caused by fluid changes in the trans-thoracic tissues, especially in the lungs, due to the patient's exercise level. An average impedance trans-thoracic value may be calculated.

In one embodiment, the impedance values may be measured over a predetermined period of time and an average value may be determined. For example, this period of time may range from 10 to 100, 30 to 80 and 50 to 70 seconds. In one embodiment of the invention, the impedance values are measured over a period of 60 seconds. Alternatively, the impedance values may be measured over a predetermined number of breathing cycles and an average value may be determined. For example, the values may be measured over a range of 1 to 5 or 2 to 4 breathing cycles. In one embodiment of the invention, the impedance values are measured over 3 breathing cycles. The interval for measuring impedance values may be determined and set by a physician, may be based on the patient's medical history, may be a preprogrammed interval, may be selected from a look-up table or database, or calculated based on data gathered by IMD 10.

As seen at Block 150, the sensed impedance values may also be filtered or otherwise processed. In one embodiment of the invention, coughing is detected and a coughing value may be determined. This coughing value may be used to adjust the impedance value for coughing by the patient. Alternatively, the coughing value may be used as another input for quantifying and assessing the pulmonary congestion, as well as the efficiency of a particular therapy. In one embodiment of the invention, an adjustment may be made to the coughing value based on a factor of induced coughing. That is, some patients with pulmonary congestion may be taking ACE inhibitors, which sometimes induce coughing. Thus, whether or not the coughing value is induced, for example by an ACE inhibitor or other drug, may be taken into consideration as part of the coughing value. The coughing value may be determined, for example, by analyzing the higher frequency components of the impedance signals. Coughs may also be detected through a piezoelectric crystal on the device housing or through a lead-based accelerometer on a lead. The coughing value may be a preset value determined and set by a physician, may be a value based on the patient's medical history, may be selected from a look-up table or database, or calculated based on data gathered by IMD 10.

As mentioned above, the trans-thoracic impedance measurements may be taken over a series of breathing cycles. In one embodiment, a measurement or series of measurements may be collected at a given sampling frequency over a given period of time. For example, an average impedance value may be determine by collecting impedance values at a sampling frequency of 16 Hz over 6 seconds, resulting in 96 samples. Preferably, the average trans-thoracic impedance used, $Z_A$, is a running average. Of course, the particular time over which the samples are collected, as well as the frequency at which they are collected, may be altered to suit the patient and/or the desires of the physician. At Block 200, IMD 10 may calculate the average trans-thoracic impedance, $Z_A$, based on values collected at Block 100. This average trans-thoracic impedance value may also be modified based on values determined at Block 200. This calculation of the average trans-thoracic impedance value may be accomplished, for example under the control of any appropriate computer algorithm stored in a memory or a portion of a memory of microcomputer 58 in IMD 10. Such a computer algorithm may be any program capable of being stored in an electronic medium such as, by way of example only, RAM 68 or ROM 70 of IMD 10, where the contents of RAM 68 and ROM 70 may be accessed and consequently executed by microprocessor 64/microcomputer 58. This average value may then be used as a "baseline" (i.e., reference) value for determining whether and with what speed any changes, especially decreases, in trans-thoracic impedance occur. In one embodiment, these changes in trans-thoracic impedance may be due to changes in the patient's exercise level. In one embodiment of the invention, these average values may be stored as shown at Block 1200. This data may be stored, for example, in a storage location of IMD 10, including but not limited to, a location of memory 59 and/or RAM 68.

At Block 250, IMD 10 may then measure the heart rate of the patient. This may be used to determine, for example, whether the patient's exercise level has increased. This may be accomplished by measuring an increase in the heart rate of the patient. Alternatively, this may be done by using any other rate responsive measuring means. This may be done by using one or more rate responsive sensors, such as, for example, sensor 11 as described above or an array of similar sensors. This may also be measured by using any suitable sensor, such as, for example, a QT sensor, as is known in the art. If the patient's heart rate, and thus, corresponding exercise level has not increased, IMD 10 may continue to collect impedance values, returning to Block 100. As seen at Block 300 if the patient's exercise level has increased, IMD 10 may then determine the lowest trans-thoracic impedance value $Z_{LOW}$, as illustrated in Block 400. This determination of lowest trans-thoracic impedance value may be accomplished, for example under the control of any appropriate computer algorithm stored in a memory or a portion of a memory of microcomputer 58 in IMD 10. Such a computer algorithm may be any program capable of being stored in an electronic medium such as, by way of example only, RAM 68 or ROM 70 of IMD 10, where the contents of RAM 68 and ROM 70 may be accessed and consequently executed by microprocessor 64/microcomputer 58.

As seen at Block 450, this $Z_{LOW}$ value may be used as a reference to determine if the trans-thoracic impedance is continuously decreasing. Such continuous decreasing may occur when the patient commences an intense exercise. The $Z_{LOW}$ value may also be used as a reference to determine if the trans-thoracic impedance is reaching a steady, but significantly lower baseline, which may be the case when the patient commences an otherwise normal exercise. The $Z_{LOW}$ value may also be used to determine if the impedance is returning back to the "baseline" $Z_A$. The $Z_{LOW}$ value may be stored as seen at Block 1200. In one embodiment of the invention, the $Z_{LOW}$ value is stored at a predetermined time. Alternatively the $Z_{LOW}$ value may be stored when a predetermined "trigger" indicates that storage should occur. These $Z_{LOW}$ values may be stored, for example, with corresponding times and levels of exercise. Such values may be used by a physician to determine an indication of the extent of the pulmonary congestion. This data may be stored, for example, in a storage location of IMD 10, including but not limited to, a location of memory 59 and/or RAM 68. If the measured impedance value continues to move to this $Z_{LOW}$ value it may be interpreted as a severe degree of pulmonary congestion, potentially leading to edema, as shown at Block 1100. As a result, therapy should be delivered immediately.

In Block 500, the diagnosis may further be confirmed by using IMD 10 to determine whether the measured impedance value is tending to a constant "baseline" trans-thoracic impedance value $Z_{BASE}$. This determination may be accomplished, for example under the control of any appropriate computer algorithm stored in a memory or a portion of a memory of microcomputer 58 in IMD 10. Such a computer algorithm may be any program capable of being stored in an electronic medium such as, by way of example only, RAM 68 or ROM 70 of IMD 10, where the contents of RAM 68 and ROM 70 may be accessed and consequently executed by microprocessor 64/microcomputer 58. If the measured impedance value does not tend to this $Z_{BASE}$ value it may be interpreted as a severe degree of pulmonary congestion, potentially leading to edema, as shown at Block 1100. As a result, therapy should be delivered immediately.

As indicated at Block 900, the patient may be treated. In one embodiment of the invention, the patient is treated if severe pulmonary congestion is indicated as described above. Such therapy may include systemic and/or diastolic drugs, as well as electrical stimulation of heart 8. Therapy may be administered, for example, automatically, for example electrical stimulation or drug therapy delivered automatically. Therapy may also be administered manually, for example, by alerting the physician that therapy is necessary. The therapy of the patient may continue, for example, until the patient's heart rate decreases, as shown at Block 1000. The patient's heart rate may decrease, for example, as the patient's exercise level decreases.

If the measured impedance is approaching trans-thoracic impedance baseline value $Z_{BASE}$, IMD 10 may then calculate a maximum trans-thoracic impedance difference, $Z_{MAX}$, as shown at Block 600. This calculation of maximum trans-thoracic impedance difference may be accomplished, for example under the control of any appropriate computer algorithm stored in a memory or a portion of a memory of microcomputer 58 in IMD 10. Such a computer algorithm may be any program capable of being stored in an electronic medium such as, by way of example only, RAM 68 or ROM 70 of IMD 10, where the contents of RAM 68 and ROM 70 may be accessed and consequently executed by microprocessor 64/microcomputer 58. In one embodiment of the invention, $Z_{MAX}$ illustrates the difference between the lowest impedance sensed while the patient is commencing exercise, or otherwise increasing his heart rate, and the baseline trans-thoracic impedance value, $Z_{BASE}$. As discussed above, this parameter indicates the degree of fluid which masses in the thoracic region due to the patient's exercise level, i.e., the degree to which the patient has pulmonary congestion. Using this value, $Z_{MAX}$, and by comparing $Z_{BASE}$ to $Z_A$, IMD 10 may be used to accurately determine whether therapy should be delivered to the patient. In one embodiment of the invention, impedance values being collected may be compared to predetermined values as indicated at Block 700. Values of $Z_{MAX}$ may also be compared to predetermined values as indicated at Block 750. If the values are larger than a predetermined difference value, as provided in Block 700, a moderate degree of pulmonary congestion may be determined as indicated at Block 800. These predetermined values may also be stored values from a database. Alternatively, these values may be determined from previously stored impedance measurements. In one embodiment of the invention, the predetermined values are determined through extensive clinical testing and the collection of data from patients without pulmonary congestion and from patients with pulmonary congestion.

In one embodiment of the invention, therapy may then be delivered to treat the mild congestion as indicated at Block 900. Such therapy may include systemic and/or diastolic drugs, as well as electrical stimulation of heart 8. Therapy may be administered, for example, automatically, for example electrical stimulation or drug therapy delivered automatically. Therapy may also be administered manually, for example, by the physician. The therapy of the patient may continue, for example, until the patient's heart rate decreases, as shown at Block 1000. The patient's heart rate may decrease, for example, as the patient's exercise level decreases.

As stated above, in Blocks 700, 750, IMD 10 may quantify the degree of pulmonary congestion. This may be accomplished by determining whether the difference between $Z_A$ and $Z_{BASE}$ is greater than a predetermined value. In addition, IMD 10 may further determine whether $Z_{MAX}$ is greater than a second predetermined value. These predetermined values may be gathered from previously stored data, from a database of predetermined values or may be determined by the physician based on the patient's history or other factors. The information may then be used by IMD 10 to provide pulmonary edema therapy, as shown at Block 900. Such therapy may include systemic and/or diastolic drugs, as well as electrical stimulation of heart 8 or other areas of the body or any combination thereof. If such therapies are successful, then the values sensed by IMD 10 may move in a direction opposite to that shown in FIGS. 7a, b and c. That is, if a patient with severe pulmonary congestion, with a trans-thoracic impedance response resembling that shown in FIG. 7c, receives adequate therapy, the resulting curve may begin to resemble that of a patient without pulmonary congestion, for example, as illustrated in FIG. 7a. Likewise, if a patient with moderate pulmonary congestion, with a trans-thoracic impedance response resembling that shown in FIG. 7b, receives adequate therapy, the resulting curve may begin to resemble that of a patient without pulmonary congestion, for example, as illustrated in FIG. 7a. Of course additional therapies may also be delivered. Thus, an important capability of the present invention is that it allows the patient's condition to be assessed and the resulting sensed condition to be fed back into IMD 10, so that the most appropriate therapy may be delivered, both in terms of the time or frequency at which the therapy is delivered, as well as the form, e.g., strength or dosage. In other words, by evaluating at Block 1000, the efficacy of the therapy delivered at Block 900, the most appropriate therapy corresponding to the patient's current trans-thoracic impedance response may be delivered.

In the embodiments of the invention seen in FIG. 8, the parameters determined include: trans-thoracic impedance values, average trans-thoracic impedance values, coughing values, heart rate values, lowest trans-thoracic impedance values, baseline trans-thoracic impedance values, and maximum trans-thoracic impedance values. One or any suitable combination of these parameters may be varied in accordance with the present invention. Alternatively, one or more of these parameters may be set at a desired value while one or more other parameters are varied in accordance with the present invention. Moreover, although the parameters are shown as being determined in a given order, these parameters may be determined in any combination and in any order in accordance with the present invention.

The preceding specific embodiments are illustrative of the practice of the invention. It is to be understood, therefore, that other expedients known to those skilled in the art or disclosed herein, may be employed without departing from the invention or the scope of the appended claims. For example, the present invention is not limited to a method of diagnosing pulmonary congestion in a mammalian heart. The present invention is also not limited to the diagnosis of pulmonary congestion, per se, but may find further application as a measuring means. The present invention further includes within its scope methods of making and using the diagnostic means described hereinabove.

In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts a nail and a screw are equivalent structures.

We claim:

1. A method of diagnosing pulmonary congestion, comprising:
    sensing at least one decrease in a trans-thoracic impedance value from a baseline trans-thoracic impedance value;
    sensing at least one increase in a heart rate value from a baseline heart rate value; and
    diagnosing pulmonary congestion if the decrease in the trans-thoracic impedance value corresponding to the increase in the heart rate does not increase after a predetermined interval.

2. The method of claim 1, further comprising:
    determining the baseline trans-thoracic impedance value.

3. The method of claim 1, further comprising:
    determining the baseline heart rate value.

4. The method of claim 1, further comprising:
    determining the predetermined interval.

5. The method of claim 1, further comprising:
    determining the trans-thoracic impedance value.

6. The method of claim 5, wherein determining the trans-thoracic impedance value comprises:
    delivering an excitation current pulse between a first electrode and a second electrode; and
    sensing the trans-thoracic impedance between the first electrode and the second electrode.

7. The method of claim 6, wherein at least one of the first electrode and the second electrode is disposed within an atrium.

8. The method of claim 6, wherein at least one of the first electrode and the second electrode is disposed within a ventricle.

9. The method of claim 1, wherein the trans-thoracic impedance value is an average determined from a plurality of trans-thoracic impedance values.

10. The method of claim 1, wherein sensing the increase in the heart rate value comprises:
    sensing the heart rate value with an activity sensor.

11. The method of claim 1, wherein sensing the increase in the heart rate value comprises:
    sensing the heart rate value with an QT sensor.

12. The method of claim 1, wherein sensing the increase in the heart rate value comprises:
    sensing the heart rate value with a rate-responsive sensor.

13. The method of claim 1, further comprising:
    determining a lowest trans-thoracic impedance value.

14. The method of claim 13 wherein the trans-thoracic impedance value tends toward the lowest-trans-thoracic impedance value, comprising:
    diagnosing severe pulmonary congestion.

15. The method of claim 1, further comprising:
    determining a maximum trans-thoracic impedance value.

16. The method of claim 1, further comprising:
    determining at least one predetermined impedance value, the predetermined impedance value indicating a level of pulmonary congestion.

17. The method of claim 16, further comprising:
    determining if the decrease in the trans-thoracic impedance value is greater than the predetermined impedance value;
    determining a maximum trans-thoracic impedance value;
    determining if the decrease in the trans-thoracic impedance value is greater than the maximum trans-thoracic impedance value; and
    diagnosing mild pulmonary congestion if the decrease is greater than the predetermined impedance value but less than the maximum trans-thoracic impedance value.

18. The method of claim 1, further comprising:
    determining a degree of pulmonary congestion based on the decrease in the trans-thoracic impedance value.

19. The method of claim 18, further comprising:
    administering therapy based on the degree of pulmonary congestion.

20. The method of claim 19, wherein administering therapy further comprises:
    transmitting an electrical stimulation to the cardiac tissue.

21. The method of claim 19, wherein administering therapy further comprises:
    providing an alert indicating that therapy should be administered.

22. The method of claim 19, wherein administering therapy further comprises:
    delivering at least one drug to the cardiac tissue.

23. The method of claim 22, wherein the drug is a nitrate.

24. An implantable medical device comprising:
    a processor;
    at least one impedance sensor operably connected to the processor, wherein
        the sensor senses at least one decrease in a trans-thoracic impedance value from a baseline trans-thoracic impedance value, the trans-thoracic impedance value corresponding to an increase in heart rate and the processor diagnoses pulmonary congestion if the decrease in the trans-thoracic impedance value does not increase after a predetermined interval.

25. The device of claim 24 further comprising:
    at least one pacing lead.

26. The device of claim 24 further comprising:
    a first electrode; and
    a second electrode wherein
        the decrease in the trans-thoracic impedance is sensed by delivering an excitation current pulse between the first and the second electrode.

27. The device of claim 24 wherein the processor determines the trans-thoracic impedance as an average of impedance values over a predetermined interval.

28. The device of claim 24 further comprising:
    a rate responsive sensor to determine heart rate.

29. The device of claim 24 further comprising:
a QT sensor to determine heart rate.
30. The device of claim 24 further comprising:
an activity sensor to determine heart rate.
31. The device of claim 24 further comprising:
an alert to indicate therapy should be administered.
32. The device of claim 24, further comprising:
drug delivery means.
33. The device of claim 24, further comprising:
at least one stimulating lead.
34. An implantable medical system, comprising:
means for sensing at least one decrease in a trans-thoracic impedance value from a baseline trans-thoracic impedance value;
means for sensing at least one increase in a heart rate value from a baseline heart rate value; and
means for diagnosing pulmonary congestion if the decrease in the trans-thoracic impedance value corresponding to the increase in the heart rate does not increase after a predetermined interval.
35. The system of claim 34, further comprising:
means for determining the baseline trans-thoracic impedance value.
36. The system of claim 34, further comprising:
means for determining the baseline heart rate value.
37. The system of claim 34, further comprising:
means for determining the predetermined interval.
38. The system of claim 34, further comprising:
means for determining the trans-thoracic impedance value.
39. The system of claim 34, further comprising:
means for delivering an excitation current pulse between a first electrode and a second electrode; and
means for sensing the trans-thoracic impedance between the first electrode and the second electrode.
40. The system of claim 34, further comprising:
means for determining an average trans-thoracic impedance value.
41. The system of claim 34, further comprising:
means for sensing the heart rate value with an activity sensor.
42. The system of claim 34, further comprising:
means for sensing the heart rate value with an QT sensor.
43. The system of claim 34, further comprising:
means for sensing the heart rate value with a rate-responsive sensor.
44. The system of claim 34, further comprising:
means for determining a lowest trans-thoracic impedance value.
45. The system of claim 34, further comprising:
means for diagnosing severe pulmonary congestion.
46. The system of claim 34, further comprising:
means for determining a maximum trans-thoracic impedance value.
47. The system of claim 34, further comprising:
means for determining at least one predetermined impedance value, the predetermined impedance value indicating a level of pulmonary congestion.
48. The system of claim 47, further comprising:
means for determining if the decrease in the trans-thoracic impedance value is greater than the predetermined impedance value;
means for determining a maximum trans-thoracic impedance value;
means for determining if the decrease in the trans-thoracic impedance value is greater than the maximum trans-thoracic impedance value; and
means for diagnosing mild pulmonary congestion if the decrease is greater than the predetermined impedance value but less than the maximum trans-thoracic impedance value.
49. The system of claim 34, further comprising:
means for determining a degree of pulmonary congestion based on the decrease in the trans-thoracic impedance value.
50. The system of claim 34, further comprising:
means for administering therapy based on the degree of pulmonary congestion.
51. The system of claim 34, further comprising:
means for transmitting an electrical stimulation to the cardiac tissue.
52. The system of claim 34, further comprising:
means for providing an alert indicating that therapy should be administered.
53. The system of claim 34, further comprising:
means for delivering at least one drug to the cardiac tissue.
54. A computer usable medium including a program for diagnosing pulmonary congestion, comprising:
computer program code that senses at least one decrease in a trans-thoracic impedance value from a baseline trans-thoracic impedance value;
computer program code that senses at least one increase in a heart rate value from a baseline heart rate value; and
computer program code that diagnoses pulmonary congestion if the decrease in the trans-thoracic impedance value corresponding to the increase in the heart rate does not increase after a predetermined interval.
55. The program of claim 54, further comprising:
computer program code that determines the baseline trans-thoracic impedance value.
56. The program of claim 54, further comprising:
computer program code that determines the baseline heart rate value.
57. The program of claim 54, further comprising:
computer program code that determines the predetermined interval.
58. The program of claim 54, further comprising:
computer program code that determines the trans-thoracic impedance value.
59. The program of claim 54, further comprising:
computer program code that delivers an excitation current pulse between a first electrode and a second electrode; and
computer program code that senses the trans-thoracic impedance between the first electrode and the second electrode.
60. The program of claim 54, further comprising:
computer program code that determines an average trans-thoracic impedance value.
61. The program of claim 54, further comprising:
computer program code that senses the heart rate value with an activity sensor.
62. The program of claim 54, further comprising:
computer program code that senses the heart rate value with an QT sensor.

63. The program of claim 54, further comprising:

computer program code that senses the heart rate value with a rate-responsive sensor.

64. The program of claim 54, further comprising:

computer program code that determines a lowest trans-thoracic impedance value.

65. The program of claim 54, further comprising:

computer program code that diagnoses severe pulmonary congestion.

66. The program of claim 54, further comprising:

computer program code that determines a maximum trans-thoracic impedance value.

67. The program of claim 54, further comprising:

computer program code that determines at least one predetermined impedance value, the predetermined impedance value indicating a level of pulmonary congestion.

68. The program of claim 47, further comprising:

computer program code that determines if the decrease in the trans-thoracic impedance value is greater than the predetermined impedance value;

computer program code that determines a maximum trans-thoracic impedance value;

computer program code that determines if the decrease in the trans-thoracic impedance value is greater than the maximum trans-thoracic impedance value; and computer program code that diagnoses mild pulmonary congestion if the decrease is greater than the predetermined impedance value but less than the maximum trans-thoracic impedance value.

69. The program of claim 54, further comprising:

computer program code that determines a degree of pulmonary congestion based on the decrease in the trans-thoracic impedance value.

70. The program of claim 54, further comprising:

computer program code that administers therapy based on the degree of pulmonary congestion.

71. The program of claim 54, further comprising:

computer program code that transmits an electrical stimulation to the cardiac tissue.

72. The program of claim 54, further comprising:

computer program code that provides an alert indicating that therapy should be administered.

73. The program of claim 54, further comprising:

computer program code that delivers at least one drug to the cardiac tissue.

* * * * *